United States Patent [19]

Umezawa et al.

[11] Patent Number: 4,533,548
[45] Date of Patent: Aug. 6, 1985

[54] **ACIDIC POLYSACCHARIDE CH-1 ISOLATED FROM *CHLORELLA PYRENOIDOSA* AND THE USE THEREOF**

[75] Inventors: Iwao Umezawa, Tokyo; Kanki Komiyama, Kanagawa, both of Japan

[73] Assignee: Kitasato Institute, Tokyo, Japan

[21] Appl. No.: 441,630

[22] Filed: Nov. 15, 1982

[30] Foreign Application Priority Data

Dec. 2, 1981 [JP] Japan .................... 56-192899

[51] Int. Cl.³ .................. A01N 31/00; A61K 31/70; C12R 1/89; C12P 19/04
[52] U.S. Cl. .................. 514/54; 424/88; 435/101; 435/946; 536/1.1
[58] Field of Search .......... 424/195, 180, 88; 435/946, 101; 260/112 R; 536/1

[56] References Cited

PUBLICATIONS

Umezawa et al., *Chemical Abstracts*, v. 98, No. 83293v, "Anacidic Polysaccharide, Cholon A from *Chlorella pyrenoidosa* I. Physiochemical and Biological Properties".
White et al., *Biochimica et Biophysica Acta*, pp. 117–126, "An Acid Polysaccharide from the Cell Wall of *C. pyrenoidosa*".
Shino, Kunihiko *Chem. Abstracts*, v. 93, 1980, 3840e, "Cell Wall of Chlorella and its Polysaccharides".
Majia, F. Z. et al., *Chem. Abstracts*, v. 87, 1977, 164108p.
Takeda et al., *Chem. Abstracts*, v. 89, 1978, 10319y.
Mutai, Masahiko et al., *Chem. Abstracts*, v. 87, 1977, 157180c, "Polysaccharides from *C. regularis* as Anti--Tumor Agents".

*Primary Examiner*—Thomas Wiseman
*Assistant Examiner*—Robin Teskin
*Attorney, Agent, or Firm*—Holman & Stern

[57] ABSTRACT

A new acidic polysaccharide is isolated from a culture of cells of the algae *Chlorella pyrenoidosa*. The process for producing this polysaccharide is also disclosed. This substance exhibits antitumor activity and antiviral activity and induces the production of interferon.

7 Claims, 3 Drawing Figures 0.1M PYRIDINE-ACETIC ACID pH 5.0
200V (4mA), 20 MIN.

ACIDIC POLYSACCHARIDE CH-1 ISOLATED FROM *CHLORELLA PYRENOIDOSA* AND THE USE THEREOF

BACKGROUND OF THE INVENTION

Many polysaccharides having either antitumor activity or the capacity for inducing interferon are known, and some, such as the antitumor agent PSK, have been commercially employed. However, substances having both properties of antitumor activity and clear interferon-inducible activity are not known in the art.

SUMMARY OF THE INVENTION

The invention comprises a new physiologically active substance herein designated CH-1. CH-1 is characterized as an acidic polysaccharide having a sugar content comprising a major proportion of rhamnose and minor amounts of galactose, arabinose, glucose, and glucuronic acid. No protein is detectable by Folin-Lowry color analysis. Both antitumor activity and interferon (IF) inducible activity are exhibited by CH-1. The substance is produced by extraction and isolation from a culture broth of cells of the genus Chlorella, preferably cells of *Chlorella pyrenoidosa*, or mutant strains thereof.

While an antitumor substance described in Japanese Patent Unexamined Publication 52-79016 has previously been isolated from *Chorella regularis*, this substance has no known interferon-inducing capability. Further, the known substance has a polysaccharide content of primarily glucose (95±2%), with only trace amounts of rhamnose and galactose, and a protein content of 3.6%.

DETAILED DESCRIPTION OF THE INVENTION

Chlorella used in the present invention comprises a unicellular algae well-known and widely distributed in the natural world. Preferably, the cell culture used in the present invention is a culture of *Chlorella pyrenoidosa*, including artificial mutant strains prepared by ultraviolet, X-ray, radiation or chemical mutagens, and natural mutant strains. In general, any strain of Chlorella which produces CH-1 can be used in the present invention. According to the present invention, cells of the genus Chlorella are cultured in a suitable medium. Nutrient media comprising acetic acid; carbon dioxide; calcium, magnesium, and potassium salts; and, if necessary, other carbon sources such as glucose; nitrogen sources such as urea; and vitamins, are suitable. Cultivation is usually carried out aseptically in a sealed tank under aerobic conditions. Visible light, for example, sunlight or fluorescent light, is applied.

CH-1 is extracted by hot water from the cultured cells or spray dried cells. Extraction is generally performed at about 80°–90° C. for about one (1) hour. The extract or its concentrate is treated with a water-miscible organic solvent to precipitate the material. Preferred water miscible solvents are lower alcohols, for example, $C_1$–$C_4$ alkanols such as methanol and ethanol. Preferred concentrations of solvent are between 40–80% by weight.

The resulting precipitate is collected by centrifugation, dissolved in water and dialyzed with a semi-permeable membrane such as cellophane tubing to remove low molecular impurities.

The dialysate is treated by adsorption chromatography and gel filtration to purify the CH-1. For example, the dialyzate is adsorbed on a column of DEAE-cellulose and eluted with dilute alkaline solution. The eluate is neutralized, passed through a column of CM-cellulose, and the active fraction lyophilized. The lyophilizate is dissolved in water and purified by column chromatography, preferably by adsorption on a column of DEAE-sephacel, gradiently chromatographed with water and 1M NaCl/0.01N-HCl. Active fractions are collected, subjected to gel-filtration using Sephadex G-75 and lyophilized to obtain CH-1.

The CH-1 has the following physico-chemical properties:

(1) At least consisting of carbon, hydrogen, oxygen and nitrogen, and having the following elementary analysis: C: 38.49%, H: 6.07%, N: 1.39%

(2) Molecular weight: impermeable for cellophane membrane, and S=6.15, measured by ultracentrifuge at concentration of 0.2%, in 0.2M phosphate buffer pH 7.2. Rotor type: RA 60HC, 51,200 r.p.m.

(3) Melting point: colored approximately at 240° C., thereafter carbonization at higher temperature.

(4) Specific rotation: $[\alpha]_D^{29} = -9.52$ (c=1, $H_2O$).

(5) UV-spectrum: end absorption in 0.125% aqueous solution. No UV maxima or minima were found.

Figure 1:
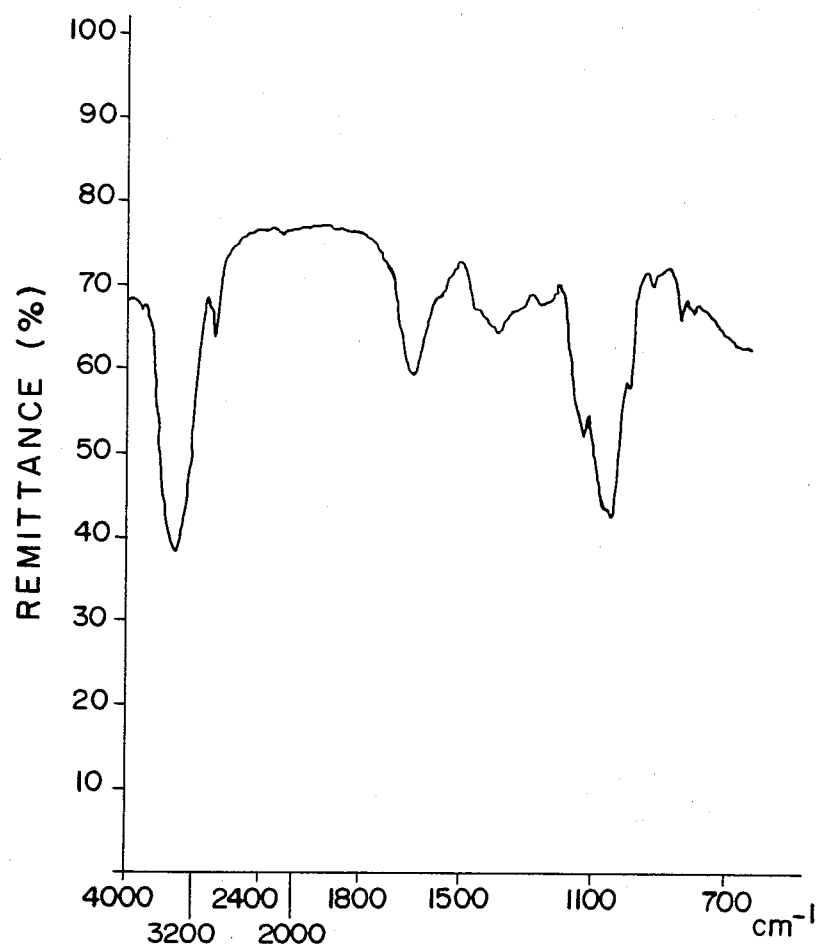
FIG. 1 is a graph of the IR-spectrum of CH-1.

(6) IR-spectrum (shown in FIG. 1): KBr tablet, absorption bands at 3420, 2930, 1640, 1380, 1125, 1065, 1040, 990, 915, 835 and 800 $cm^{-1}$.

(7) Solubility:
soluble: water
insoluble: common organic solvents, such as methanol.

(8) Color reaction:
positive: Anthrone, Molisch and carbazole-$H_2SO_4$
negative: Folin-Lowry and ninhydrin.

(9) Nature: acidic, electrophoresis on acetate membrane (FIG. 2) [electrophoresed to 0.8 cm for (+) at the condition of 0.1M pyridine-acetic acid, pH 5.0, 200 V (4 mA), 20 min.].

(10) Color: white powder.

(11) Protein: not detected (measured by Folin-Lowry color reaction).

(12) Sugar content: 53% (calculated as glucose).

Figure 3:
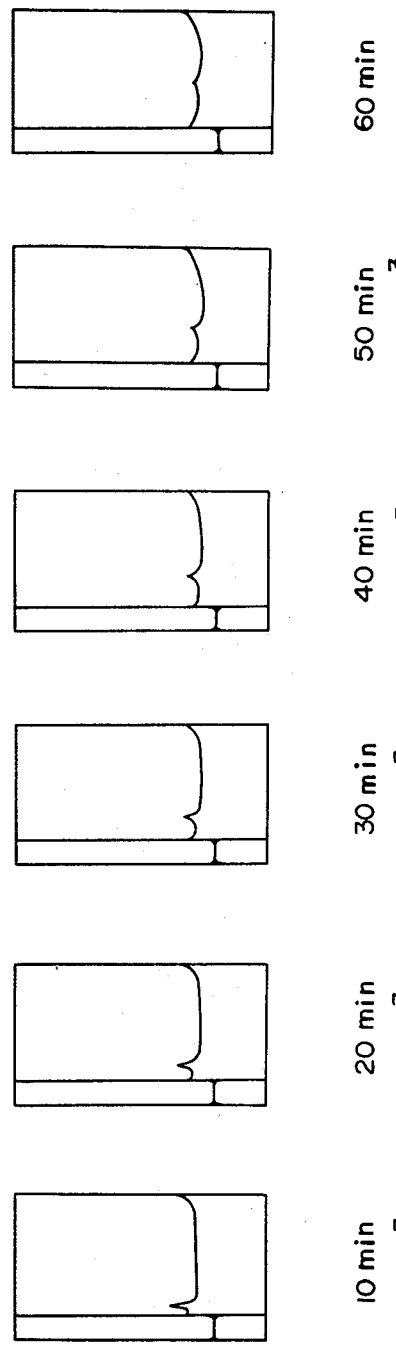
FIG. 3 is an ultracentrifugal pattern of CH-1.

(13) Ultra-centrifuge pattern (shown in FIG. 3).

(14) monosaccharide analysis: rhamnose, arabinose, glucose, galactose and glucuronic acid (detected by paper chromatography and gas chromatography after hydrolysis in 7% $H_2SO_4$, refluxed for 2 hours).

CH-1 exhibits interferon inducible activity both in vitro and in vivo, as assayed by the plaque reduction method following challenge with vesicular stomatitis virus (VSV). Further, CH-1 is useful in controlling viral infection, as evidenced by inhibition of vaccinia infection of mouse tail skin after treatment with CH-1 followed by challenge with vaccinia virus. Additionally CH-1 exhibits antitumor activity in in vivo mouse studies against mouse leukemia P-388 and S-180 solid tumors.

The following Examples are included as illustrative of the invention.

EXAMPLES

Example I. Preparation of CH-1

Spray-dried powder (1 kg) of *Chlorella pyrenoidosa* was extracted with hot water (5 lit.) at 80°–90° C. for one (1) hour. Extract was centrifuged at 7000 r.p.m. for 20 minutes. Methanol was added to the supernatant solution up to 40% concentration and stood over-night at 5° C.; the precipitate was collected by centrifuging at 9000 r.p.m. for 20 minutes. Precipitate was dissolved in water and the aqueous solution in a cellophane tube was dialyzed against deionized flowing water over-night. Dialyzate was adsorbed in a column (6.4×39 cm) of DEAE-cellulose, equilibrated with 0.005M phosphate buffer (pH 6.0), and eluted with 0.05N-NaOH. Each 10 ml fraction was checked for IF inducible activity and collected active fractions were neutralized with 1N-HCl. The solution was passed through a column (4×15 cm) of CM-cellulose, and the eluate concentrated and lyophilized. Crude powder dissolved in a small amount of water was adsorbed in a column (2.5×50 cm) of DEAE-sephacel and was eluted by gradient elution with water (500 ml) and 1M NaCl/0.01N-HCl (500 ml). Each 10 ml fraction was checked by anthrone-$H_2SO_4$ and the fractions containing a high concentration of saccharide were collected, neutralized by 0.02N-NaOH, and then dialyzed with cellophane tube against tap water over-night. Dialyzate was passed through a column (5×70 cm) of Sephadex G-75. The eluate was lyophilized to obtain a white powder of CH-1 (200 mg).

Example II. Induction Of Interferon By CH-1

(1) Assay method A (in vitro)

A rabbit (Japanese white) was bled by arteriotomy. The extirpated spleen was trypsinized to prepare suspended cells (2–5×10$^7$ cells). The spleen cells were incubated with CH-1 from Example I at 25° C. for 24 hours, centrifuged, the supernatant collected. Interferon titer in the medium was determined by assay of the IF titer by the method of plaque (50%) reduction, using RK13 rabbit kidney cell-line culture and VSV as aggression virus.

Results were as follows:

| Sample concentration (μg/ml): | 10 | 1 | 0.1 | 0.01 |
|---|---|---|---|---|
| IF titer (μ): | 49 | 34 | 20 | — |

(2) Assay method B (in vivo)

After intravenous injection of ddy mice, four (4) weeks of age, with 100 mg/kg of CH-1, the mice were bled and the interferon titer in the serum was determined. The bleeding times and IF serum titer was as follows:

| Bleeding time: | 2 hr later | 5 hr later |
|---|---|---|
| IF titer (μ): | 240 | 15 |

The plaque reduction method employed for the IF titer assay is that used in Assay method A, and is of the type described by Wagner, *Bacteriol. Rev.* 27:72–86 (1963).

Example III. Inhibition Of Virus Activity By CH-1

Assay method:

CH-1 was administered intravenously into the tail veins of ddy mice, and after 2–12 hours the mice were challenged with vaccinia virus intravenously injected into the tail vein. The number of pocks appearing in the tail skin were counted at day 8 after the challenge.

The results are set forth in the following Table:

| Inhibitory Activity On Virus Infection | | |
|---|---|---|
| Dose (mg/kg) | Treatment Schedule | Mean Numbers Of Pock (five mice) |
| control | — | 58.7 |
| 100 | −2 hr. | 1 |
| 25 | −2 hr. | 1.6 |
| 100 | −6 hr. | 4 |
| 25 | −6 hr. | 26 |

Example IV. Antitumor Activity Of CH-1

(1) Activity against mouse leukemia P-388

CDF$_1$ mice were inoculated intraperitoneally with P-388 cells, 1×10$^2$, and were treated daily from days 1 to 15 with CH-1.

| | Result: | |
|---|---|---|
| Dose (mg/kg/day) | Mean Survival Days (four mice) | Increased Life Span (%)* |
| control | 15 | 0 |
| 50 | 16.8 | 8 |
| 250 | 19.5 | 26 |

*Increased life span (%) = $\frac{\text{mean survival days (treated)}}{\text{mean survival days (control)}} \times 100 - 100$ (2) Activity against S-180 solid tumor ICR-mice were inoculated subcutaneously with Sarcoma-180 (1×10$^7$) cells on day 0, and CH-1 was successively administered intraperitoneally on days 1–9, once per day, with the following results:

| Dose (mg/kg/day) | Mean Life Span (days, 5 mice) | Increased Life Span (%)* |
|---|---|---|
| — | 42 | 0 |
| 50 | 50 | 19 |
| 250 | 61 | 45 |

*Increased life span (%) = $\frac{\text{mean survival days (treated)}}{\text{mean survival days (control)}} \times 100 - 100$

Figure 2:
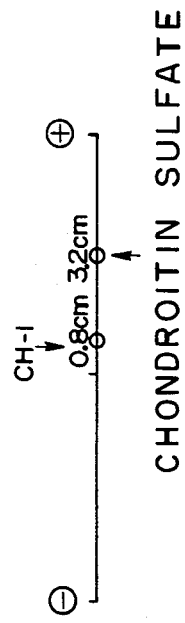
FIG. 2 is a graph of the electrophoretic pattern of CH-1 on acetate membrane.

What is claimed is:

1. An acidic polysaccharide having the following properties:
   (a) consisting of carbon, hydrogen, oxygen and nitrogen with an approximate elementary analysis of O: 54.05%; C: 38.49%; H: 6.07%; and N: 1.39%;
   (b) a sedimentation coefficient of $S_{20,w} = 6.15$ S when determined by ultracentrifugation;
   (c) impermeability to cellophane membrane,
   (d) a melting point characterized by coloration at about 240° C. with carbonization at higher temperatures;
   (e) a specific rotation of $[\alpha]_D^{29} = -9.52$ (c=1, $H_2O$);
   (f) solubility in water, and insolubility in methanol;
   (g) a positive color reaction with anthrone, Molisch, and carbazole-$H_2SO_4$ and a negative color reaction with Folin-Lowry and ninhydrin;
   (h) no detectable protein as measured by Folin-Lowry color reaction test;

(i) a monosaccharide analysis consisting of rhamnose, galactose, arabinose, glucose and glucuronic acid when detected by paper chromatography and gas chromatography after hydrolysis of said polysaccharide in 7% $H_2SO_4$ under refluxing for two hours;

(j) a UV spectrum with end absorption in 0.125% aqueous solution;

(k) an IR spectrum (KBr tablet) with absorption bands at 3420, 2930, 1640, 1380, 1125, 1065, 1040, 990, 915, 835 and 880 $cm^{-1}$;

(l) an electrophoretic pattern on acetate membrane as shown in FIG. 2, electrophoresced to 0.8 cm for (+) with 0.1M pyridine-acetic acid at pH 5.0, 200 V (4 mA) for 20 minutes;

(m) an ultra-centrifuge pattern as shown in FIG. 3;

(n) being obtained as a white powdery precipitate; and (o) having a sugar content of 53% when calculated as glucose.

2. A method for the production of an acidic polysaccharide of claim 1, comprising extracting spray-dried powder of *Chlorella pyrenoidosa* with hot water at about 80°–90° C. and fractionally precipitating the polysaccharide with a water-miscible $C_1$–$C_4$ alkanol in which it is substantially insoluble.

3. The method of claim 2, wherein the precipitate is purified by dialysis of an aqueous solution thereof, followed by adsorption chromatography and gel filtration.

4. The method of claim 2, wherein the alkanol is methanol.

5. The method of claim 4, wherein the methanol concentration is about 40 to 80% by weight.

6. A process according to claim 3, wherein the adsorbent for adsorption chromatography is DEAE-cellulose or CM-cellulose.

7. A method of inducing in a mammalian host a substance having the capacity to inhibit plaque formation of vesicular stomatitis virus on RK13 rabbit kidney cell-line culture comprising administering to a mammal the polysaccharide of claim 1 in an amount sufficient to induce said substance.

* * * * *